United States Patent [19]

Hubbs

[11] Patent Number: 5,144,073
[45] Date of Patent: Sep. 1, 1992

[54] PROCESS FOR PREPARATION OF DIPEPTIDES

[76] Inventor: John C. Hubbs, Rte. 10, Box 354, Kingsport, Tenn. 37664

[21] Appl. No.: 406,994

[22] Filed: Sep. 14, 1989

Related U.S. Application Data

[63] Continuation-in-part of Ser. No. 239,494, Aug. 31, 1988, abandoned.

[51] Int. Cl.$^5$ .......................................... C07C 126/00
[52] U.S. Cl. ..................... 564/164; 544/385; 560/37; 560/40; 560/42; 564/168
[58] Field of Search .............. 564/164, 168; 560/40, 560/37, 42

[56] References Cited

U.S. PATENT DOCUMENTS

| | | | |
|---|---|---|---|
| 4,293,648 | 10/1981 | Davino | 435/70 |
| 4,634,790 | 1/1987 | Shinohara et al. | 560/40 |
| 4,668,625 | 5/1987 | Cambiaghi et al. | 435/70 |
| 4,677,220 | 6/1987 | Tou et al. | 560/40 |

FOREIGN PATENT DOCUMENTS

| | | |
|---|---|---|
| 196866 | 10/1986 | European Pat. Off. |
| 220028 | 4/1987 | European Pat. Off. |
| 62-074296 | 4/1987 | Japan |

OTHER PUBLICATIONS

T. Kanmera et al., *Int. J. Peptide Protein Res.*, 16, 280 (1980).
T. Kanmera et al., *Tetrahedron Letters*, 46, 4483 (1979).
Y. Hashimoto et al., *Int. J. Peptide Protein Res.*, 21, 11 (1983).
S. Lee et al., *Int. J. Peptide Protein Res.*, 13, 207 (1979).
H. Poisel et al., *Chem. Ber.*, 106, 3408 (1973).
B. W. Bycroft et al., J.C.S. Chem. Comm., 616, 988, 989 (1975).
R. Brown et al., *J. Org. Chem.*, 30, 277 (1965).
J. H. Birkinshaw et al., *Biochem. J.*, 85, 523 (1962).
C. Shin et al., *Heterocycles*, 14 (11), 1767 (1980).
S. Akabori et al., *Proc. Japan Acad.*, 27 (1), 7 (1951).
K. Blaha, *Collection Czechoslov. Chem. Commun.*, 34, 4000 (1969).
C. Gallina et al., *Tetrahedron Letters*, 14, 1135 (1973).
N. Izumiya et al., *J.A.C.S.*, 99:25 (1977).
T. Ueda et al., *Bull. Chem. Soc. Jpn.*, 56, 568 (1983).
M. Bergmann et al., *J. Biol. Chem.*, 535 (1944).
R. H. Mazur et al., *Dev. Sweeteners*, 1, 125 (1979).
J. D. Higginbotham et al., *Sens. Prop. Foods, [Ind.-Univ. Co-op. Symp.]* 129 (1976).

*Primary Examiner*—C. Warren Ivy
*Assistant Examiner*—James H. Turnipseed
*Attorney, Agent, or Firm*—Mark A. Montgomery; William P. Heath, Jr.

[57] ABSTRACT

Disclosed is a process for synthesis of a dipeptide such as N-acetyl-L-α-aspartyl-L-phenylalanine methyl ester wherein one amino acid serves as a chiral template which allows for synthesis of a second amino acid residue to form said dipeptide. The process involves several novel steps such as a nucleophile addition step. In addition, several novel intermediates are described.

8 Claims, No Drawings

PROCESS FOR PREPARATION OF DIPEPTIDES

This application is a continuation-in-part of copending application U.S. Ser. No. 239,494, filed Aug. 31, 1988 now abandoned.

FIELD OF INVENTION

The present invention concerns a process for synthesis of a dipeptide wherein one amino acid serves as a chiral template which allows for synthesis of a second amino acid residue to form said dipeptide.

BACKGROUND OF THE INVENTION

Alpha-amino-acids are the building blocks of proteins and are therefore essential for life itself. Amino acids can be either of the type found in protein of biological sources (so called naturally occurring) or can be of other types that are synthesized chemically (so called synthetic amino acids). Dipeptides made from amino acids of either the naturally occurring type or the synthetic type have a multitude of uses including use as a nutritional source or intermediates therefor and use as building blocks for various biologically active proteins (e.g., see for example, C. Y. Bowers, et. al., European Patent Application WO 87/06835). One particularly economically important use of certain dipeptides or derivatives thereof is their use as an artificial sweetener (e.g., see R. H. Mazur, A. Ripper, Dev. Sweeteners, 1, 125 (1979)).

Alpha-amino acids typically have one asymmetric carbon atom and therefore can be either in the L or D form. Dipeptides can therefore exist as either one or the other (or a mixture) of two diastereomeric forms. Each of the two diastereomeric forms of a dipeptide can exist as either one or the other (or as a pair) of two enantiomeric forms. For various applications and in particular for sweetness it is often desirable to have only one of the diastereomeric and enantiomeric forms of a dipeptide. Therefore processes which can produce a dipeptide in a single diastereomeric form and a single enantiomeric form are highly desirable.

SUMMARY OF THE INVENTION

The present invention is directed to a process for preparation of a substantially optically pure dipeptide wherein one amino acid serves as a chiral template for the synthesis of the other amino acid. The process of the present invention employs several novel steps including a novel hydrogenation step wherein a cyclic compound having an asymmetric carbon of either L or D configuration and an unsaturated carbon-carbon double bond is converted to a cyclic compound with two asymmetric carbon atoms in substantially the cis form. Such hydrogenation step shall be referred to herein as "the hydrogenation step". More specifically, the hydrogenation step comprises contacting Compound I of the formula

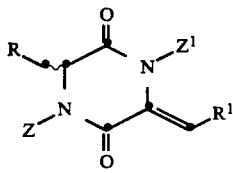

(I)

wherein R and $R^1$ are not the same and are each, independently, hydrogen, alkyl, hydroxy, aryl, $C_1$ to $C_{10}$ substituted alkyl, $C_1$ to $C_{10}$ alkoxy, $C_7$ to $C_{12}$ arylalkyl, $C_7$ to $C_{12}$ substituted arylalkyl, $C_1$ to $C_{10}$ carboxyalkyl, $C_1$ to $C_{10}$ acyl, $C_1$ to $C_{10}$ acyloxy or the like; Z and $Z^1$ are hydrogen or a nitrogen-protecting group (in most cases, it is preferred that Z is not hydrogen);

with hydrogen in the presence of a suitable catalyst and suitable solvent to form Compound II of the formula

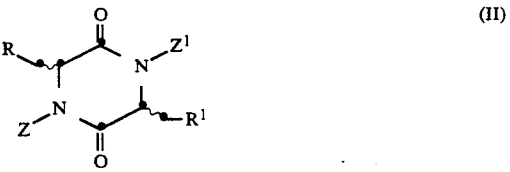

(II)

wherein the diastereomeric purity of Compound II is at least about 70% of the cis derivative, preferably at least about 90%, and most preferably at least about 95%.

The present invention also makes use of a novel step wherein the ring structure of Compound II wherein Z is not hydrogen and is a nitrogen protecting group is opened by use of a nucleophile. This nucleophilic addition step comprises contacting Compound II with a nucleophile of the formula HQ in the presence of an appropriate solvent and an acid or base, under conditions such that a compound is formed of the formula

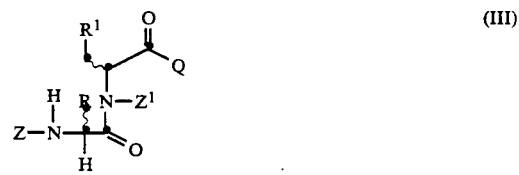

(III)

wherein R, $R^1$, and $Z^1$ and Z are as defined hereabove, provided that in the conversion of II to III the ability of the Z substituent to withdraw electrons is greater than that of the $Z^1$ substituent, and Q is a group capable of being displaced by a nitrogen-containing nucleophile. In the case of Compound III, although the Q substituent is capable of being displaced by a nitrogen-containing nucleophile, based on the principle of microscopic reversibility, the actual occurrence of such displacement is not generally preferable.

The diastereomeric purity of Compound III is at least about 70%, preferably at least about 90%, and most preferably at least about 95%.

The present invention also embraces novel compounds formed by the process of the present invention. Such novel compound are of the formula

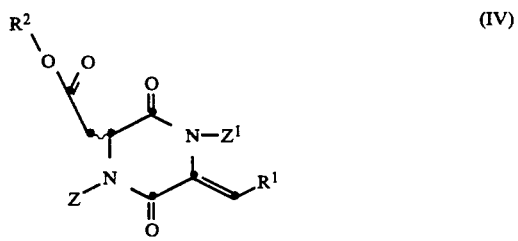

(IV)

wherein $R^2$ is hydrogen, alkyl, aryl, $C_1$ to $C_{10}$ substituted alkyl, $C_7$-$C_{12}$ arylalkyl, or the like; and Z, $Z^1$ and $R^1$ are as defined hereabove.

Other novel compounds within the scope of the present invention include cis compounds of the formula

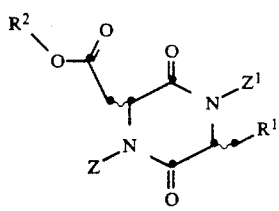

(V)

wherein $R^1$, $R^2$, Z, and $Z^1$ are as defined hereabove.

DETAILED DESCRIPTION OF THE INVENTION

The undulating lines (i.e., ~)

connecting various substituents in the formulas appearing herein indicate bonds wherein the stereochemistry of the asymmetric carbon atom of the bond is wholly or substantially in the D or L configuration. In the case where there are 2 undulating lines (bonds) in a single molecule, the asymmetric carbon atoms bearing these bonds, are each wholly or substantially of the same configuration (e.g. LL or DD). As used in this context, the term "substantially" means that at least about 70% of the desired compound is in the desired configuration; preferred is at least about 90%, and most preferred is 95%. For the cyclic compounds described herein, it is preferred that they be substantially of the cis configuration. For a cyclic compound described herein to be of substantially the cis configuration; if one substituent (e.g., on the lefthand side of the ring) is wholly or substantially of the L-configuration, the other substituent (i.e., on the righthand side of the ring) must also be wholly or substantially of the L-configuration. Conversely, if one substituent is wholly or substantially of the D-configuration, the other substituent must also be wholly or substantially of the D-configuration, for a cyclic compound described herein to be substantially of the cis configuration. The terms "D- or L-configuration" as used herein are commonly understood to those experienced in the peptide art (see for example, p. 80–83, A. L. Lehninger, *Biochemistry*, Second Ed., Worth Publishers, Inc., New York, N.Y., 1977). It is to be understood that when one or more process steps are performed consecutively wherein a cyclic compound has two asymmetric carbon atoms (alpha to the carbonyl carbon atoms) as indicated, such two asymmetric carbon atoms will be substantially in the cis form; or in the case of linear peptides, substantially in the LL or DD form. As used in this context, the term "substantially" means that at least about 70%, preferably at least about 90%, most preferred is at least about 95% of the desired compound.

As used herein the term "optical purity" or "op" refers to a single amino acid residue and can be expressed mathematically (in percentage and as an absolute value) as $$op = \left| \frac{\% \ L \ \text{isomer} - \% \ D \ \text{isomer}}{\% \ L \ \text{isomer} + \% \ D \ \text{isomer}} \right| \times 100$$

As referred to herein, with reference to cyclic dipeptides, diastereomeric purity refers to the % of cis isomer and can be expressed mathematically as % diastereomeric purity ("dp")

$$dp = \left| \frac{\text{amount of cis isomer}}{\text{amount of cis + amount of trans}} \right| \times 100$$

The term "alkyl" means straight, branched or cyclic alkyl moieties of up to 20 carbon atoms such as methyl, ethyl, n-propyl, isopropyl, n-butyl, isobutyl, sec-butyl, pentyl, hexyl, heptyl, octyl, nonyl, decyl, docecyl, methyl-cyclohexyl and the like. Preferred alkyl groups are $C_1$ to $C_6$ straight or branched chain alkyls.

The term "$C_1$ to $C_{10}$ substituted alkyl" denotes the above $C_1$ to $C_{10}$ alkyl groups that are substituted by one to four halogen, hydroxy, amino, substituted amino, sulfhydryl, substituted and/or oxidized substituted sulfhydryl, $C_1$ to $C_7$ tosyloxy, nitro, carboxy, cyano, methylsulfonylamino or $C_1$ to $C_{10}$ alkoxy groups. The substituted alkyl groups may be substituted once or up to four times with the same or with different substituents.

Examples of the above substituted alkyl groups include the cyanomethyl, nitromethyl, hydroxymethyl, trityloxymethyl, propionyloxymethyl, aminomethyl, allyloxycarboxylmethyl, allyloxycarboxylaminomethyl, carbamoyloxymethyl, methoxymethyl, ethoxymethyl, 1-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "$C_1$ to $C_{10}$ substituted alkyl" group includes the substituted methyl group, in other words, a methyl group substituted by the same substituents as the "$C_1$ to $C_{10}$ substituted alkyl" group. Examples of the substituted methyl group include groups such as hydroxymethyl, acetoxymethyl, carbamoyloxymethyl, chloromethyl, bromomethyl and iodomethyl.

The term "$C_1$ to $C_{10}$ alkoxy" as used herein denotes groups of the formula $OR^7$ wherein $R^7$ is hydrogen or alkyl. Examples of preferred $C_1$ to $C_{10}$ alkoxy groups include methoxy, ethoxy, n-propoxy, isopropoxy, butoxy and like groups.

The term "$C_1$ to $C_{10}$ acyl" or "acyl" denotes groups of the formula

containing between 1 and 10 carbon atoms, wherein $R^3$ is hydrogen, alkyl, aryl, substituted alkyl, arylalkyl, and substituted arylalkyl.

Examples of preferred $C_1$ to $C_{10}$ acyl groups are those wherein $R^3$ is a $C_1$ to $C_6$ alkyl group such as methyl (Me), ethyl (et), propyl (pr) or butyl(bu).

The term "$C_1$ to $C_{10}$ acyloxy" or "acyloxy" denotes groups of the formula

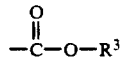

containing between 1 and 10 carbon atoms, wherein $R^3$ is as defined hereabove. Examples of preferred $C_1$ to $C_{10}$ acyloxy groups include those wherein $R^3$ is a hydrogen, $C_1$ to $C_6$ alkyl group such as methyl, ethyl, propyl, or butyl. Further examples of preferred $C_1$ to $C_{10}$ acyloxy groups include those wherein $R^3$ is a $C_7$ to $C_{12}$ arylalkyl group with the most preferred arylalkyl group being benzyl.

The term enol ester refers to a compound of the formula

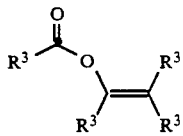

wherein each $R^3$ is independently as defined hereabove.

The term "$C_1$ to $C_{10}$ carboxyalkyl" denotes groups of the formula

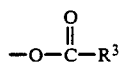

wherein R is as defined hereabove. Examples of preferred $C_1$ to $C_{10}$ carboxyalkyl groups are those wherein $R^3$ is a $C_1$ to $C_6$ alkyl group such as methyl, ethyl, propyl, or butyl.

The term "aryl" refers to aromatic groups of 3 to 50 carbon atoms which include heterocyclic rings, unsubstituted and substituted aryls. The most preferred aryl is phenyl.

The term "substituted aryl" specifies an aryl group (preferred is a phenyl group) substituted with one to four moieties chosen from the group consisting of halogen, hydroxy, protected hydroxy, cyano, nitro, $C_1$ to $C_4$ alkyl, $C_1$ to $C_4$ alkoxy, carboxy, carboxymethyl, hydroxymethyl, aminomethyl, trifluoromethyl or N-(methylsulfonylamino). Phenyl shall be alternately referred to herein by the symbol "∅" or "Ph".

Examples of the term "substituted aryl" include a mono- di- or tri(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, and the like; a mono- di- or tri(hydroxy)phenyl group such as 4-hydroxyphenyl, 3-hydroxyphenyl, 2,4-dihydroxyphenyl, the protected-hydroxy derivatives thereof, and the like; a nitrophenyl group such as 3- or 4-nitrophenol, a cyanophenyl group, for example, 4-cyanophenyl, a mono- or di(lower alkyl)phenyl group such as 4-methylphenyl, 2,4-dimethylphenyl, 2-methylphenyl, 4-(iso-propyl)-phenyl, 4-ethylphenyl, 3-(n-propyl)phenyl, and the like; a mono- di- or tri(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, and the like; 3- or 4-trifluoromethylphenyl; a mono- or dicarboxyphenyl group such as 4-carboxyphenyl; a mono- or di(hydroxymethyl)phenyl such as 3,4-di(hydroxymethyl)phenyl; a mono- or di(aminomethyl)phenyl or di(aminoethyl)phenyl such as 2-(aminomethyl)phenyl or a mono- or di-N-(methylsulfonylamino)phenyl. Also, the term "substituted phenyl" represents disubstituted or trisubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The terms "halo" and "halogen" refer to the fluoro, chloro, bromo or iodo groups.

The term "$C_7$ to $C_{12}$ arylalkyl" denotes a $C_1$ to $C_6$ alkyl group substituted at any position by an aromatic ring. Examples of such a group include phenylmethyl (benzyl), 2-phenylethyl, 3-phenyl-(n-propyl), 4-phenylhexyl, 3-phenyl-hexyl, 3-phenyl-(n-amyl), 3-phenyl-(sec-butyl), and the like. A preferred group is the benzyl group.

The term "$C_7$ to $C_{12}$ substituted arylalkyl" denotes a $C_7$ to $C_{12}$ arylalkyl group substituted on the $C_1$ to $C_6$ alkyl portion with one or two groups chosen from halogen, hydroxy, amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the aromatic group may be substituted with 1 or 2 groups chosen from halogen, hydroxy, nitro, $C_1$ to $C_4$ alkyl, $C_1$ to $C_4$ alkoxy, carboxy, carboxymethyl, hydroxymethyl, aminomethyl, or a N-(methylsulfonylamino) group. As before, when either the $C_1$ to $C_6$ alkyl portion or the aromatic portion or both are substituted, the substituents can be the same or different.

Examples of the term "$C_7$ to $C_{12}$ substituted arylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl-phenyl)-3-(aminomethyl)(n-pentyl), and the like.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring" and are non-limiting: thienyl, furyl, pyrrolyl, imidazolyl, pyrazolyl, thiazolyl, isothiazolyl, oxaxolyl, triazoly, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dioxazinyl, oxathiazinyl, tetrazinyl, thiatriazinyl, oxatriazinyl, dithiadiazinyl, imidazolinyl, tetrahydropyrimidyl, tetrazolo[1,5-b]pyridazinyl and purinyl, as well as benzo-fused derivatives, for example benzoxazolyl, benzthiaxolyl, benzimidazolyl and indolyl.

A preferred group of examples of the above heterocyclic rings are 5-membered ring systems containing a sulfur or oxygen atom and/or one to three nitrogen atoms.

Further specific examples of the above heterocyclic ring systems are 6-membered ring systems containing one to three nitrogen atoms. Such examples include pyridyl, pyrimidyl, triazinyl, pyridazinyl, and pyrazinyl.

The substituents for the optionally substituted heterocyclic ring systems, and further examples of the 5- and 6-membered ring systems discussed above, are found in W. Durckheimer et al., U.S. Pat. No. 4,278,793 issued Jul. 14, 1981, Columns 9 through 21 and Columns 33 through 188, incorporated herein by reference. (In Columns 33 through 188, examples of the term "heterocyclic ring" are included in the heterocyclic thiomethyl groups listed under heading "A".)

The more preferred aryls are phenyl, indole, naphthyl, and pyridyl; and the most preferred aryl moiety is phenyl.

The term "nitrogen-protecting group" as used in the specification and claims refers to substituents of an amide or amino group commonly employed to block or protect the amino or amide functionality while permitting other functional groups on the compound to react. Examples of such nitrogen-protecting groups include but are not limited to acetyl, the formyl group, the trityl group, the phthalimido group, the trichloroacetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-nitrobenzyloxycarbonyl, 4-cyanobenzyloxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methyl-sulfonyl)-ethoxycarbonyl, 2-(triphenylphosphono)-ethoxycarbonyl, 9-fluorenylmethoxycarbonyl ("FMOC"), t-butoxycarbonyl ("BOC"), allyloxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)-phenylsulfenyl group, the diphenylphosphine oxide group and like amino-protecting groups. The species of nitrogen-protecting group employed is not critical so long as the derivatized amide or amino group is stable to the conditions of subsequent reaction(s) on other positions of the molecule and so long as the protecting group can be removed at the appropriate point without disrupting the important functional groups on the subsequent product molecule(s). Preferred nitrogen-protecting groups are the allyloxycarbonyl, the benzyloxycarbonyl, the t-butoxycarbonyl, the formyl, the acetyl and the substituted acetyl groups. The most preferred nitrogen-protecting group is acetyl (Ac), and alpha-haloacetyl. Similar amino-protecting groups used in the peptide art are also embraced by the above term. Further examples of groups referred to by the above term are described by J. W. Barton, "Protective Groups in Organic Chemistry", J. G. W. McOmie, Ed., Plenum Press, New York, N.Y., 1973, Chapter 2; T. W. Greene, "Protective Groups in Organic Synthesis", John Wiley and Sons, New York, N.Y., 1981, Chapter 7; and R. Geiger, W. Konig, "Amine Protecting Groups," in The Peptides, V.3, E. Gross, J. Meinhofer editors, Academic Press, New York, N.Y., 1981, Chapter 1. The related term "protected nitrogen" defines an amino or amide group substituted with a nitrogen-protecting group discussed above.

Concerning the novel compounds of Formulas IV, and V, it is preferred that $R^2$ is hydrogen, alkyl, aryl, substituted $C_1$ to $C_{10}$ alkyl, $C_7$ to $C_{12}$ substituted arylalkyl or $C_7$ to $C_{12}$ alkylaryl; $R^1$ is aryl, and Z is a nitrogen protecting group. It is more preferred that $R^2$ is hydrogen, $C_1$ to $C_6$ alkyl, benzyl, or phenyl; Z is acyl or acyloxy (most preferred is acetyl, or alpha-halo-acetyl, especially alpha-chloro-acetyl), $Z^1$ is H; and $R^1$ is phenyl. In Compounds IV and V, except in the case where Z=H, the ability of the Z substituent to withdraw electrons is greater than that of the $Z^1$ substituent. For the generation of III, Z is a nitrogen-protecting group capable of activating the adjacent ring carbonyl carbon toward nucleophilic attack and $Z^1$ is H or a nitrogen-protecting group that is non-activating relative to Z. The Z substituent results in enhancement of the electrophilicity of the adjacent ring carbonyl carbon atom sufficiently enough to allow selective reaction of said adjacent ring carbon atom with an appropriate nucleophile to produce III.

In the preferred compounds described herein, R and $R^1$ are not the same and R is preferably acyloxy, $R^1$ is preferably aryl with phenyl and substituted phenyl being more preferred, and phenyl being most preferred. The preferred Z and $Z^1$ groups are generally dependent on individual compounds and are discussed thereunder.

Regarding the Q substituents of the compounds described herein, Q is capable of being displaced by a nitrogen-containing nucleophile, preferably ammonia or a substituted amine. Many Q groups are often referred to in the art as esters or active esters, and are commonly used as activating groups in the peptide art. Examples of Q groups are described by M. Bodansky in "Active Esters in Peptide Synthesis," pp. 105-196, The Peptides, I, E. Gross, J. Meienhofer, editors, Academic Press, New York, N.Y., 1981. Except for ZQ and $Z^1Q$ described hereinafter, preferred Q groups include chloro, bromo, iodo, $-SR^4$ or $-OR^4$ wherein $R^4$ is H, alkyl, aryl, $C_1$ to $C_{10}$ substituted alkyl, $C_7$ to $C_{12}$ arylalkyl, $C_7$ to $C_{10}$ aryl, and $C_1$ to $C_{10}$ aryloxy. Other Q substituents are nitrogen-containing cyclic moieties such as imidazole, succinimido, and phthalimide. For Compound III; although Q may be hydroxy (OH), Q is most preferably $C_1$ to $C_{10}$ alkoxy or $C_7$ to $C_{12}$ arylalkyl. The most preferred Q substituent for Compound III is methoxy.

A preferred process of the present invention involves several steps starting with a substantially optically pure amino acid and ending with the desired dipeptide, substantially as a single diastereomer and enantiomer. The preferred amino acids for use as starting materials in the present invention include phenylalanine, isoleucine, leucine, lysine, methionine, threonine, tryptophan, valine, alanine, aspartic acid, glutamic acid, arginine, asparagine, cysteine, glutamine, histidine, serine and tyrosine. The most preferred amino acid is aspartic acid or an ester or diester thereof, especially L-aspartic acid.

The first step ("Step 1") of the process of the present invention is a process for preparing a compound of the formula

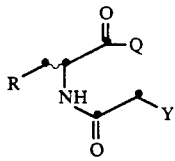

which comprises contacting a compound of the formula

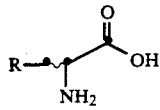

or salt thereof with either
(a) a compound of the formula

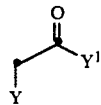

in the presence of a suitable solvent and under acidic, neutral, or basic conditions, most preferable are basic conditions, and under other conditions such that a compound is formed having the following formula

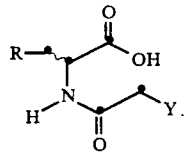

followed by reacting Compound IX, most preferably under acidic or neutral conditions, with a suitable nucleophile of the formula

HQ            (X)

in the presence of a suitable solvent under conditions such that Compound VI is formed, or
(b) a suitable nucleophile of the formula

HQ            (X)

in the presence of a suitable solvent, under weakly acidic, neutral, or basic conditions, such that there is formed a compound of the formula

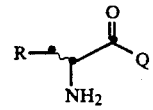

or salt thereof, followed by reacting Compound XI with Compound VIII in a suitable solvent under conditions such that Compound VI is formed;

wherein Q and R are as defined hereinbefore; and Y is a group capable of undergoing nucleophilic displacement or is amino or an amino group substituted with one or two nitrogen-protecting groups, and $Y^1$ is a group capable of undergoing nucleophilic displacement.

$Y^1$ groups are capable of undergoing nucleophilic displacement upon reaction with compound VII or compound XI. Examples of such groups include halo and alcohol leaving groups known in the art such as tosylates and mesylates.

Suitable solvents for Step 1 as well as for the steps that follow are those solvents capable of solubilizing the reactants sufficiently enough to allow the desired process step to proceed without significant adverse effects.

Suitable solvents for Step 1 include polar or nonpolar, protic or aprotic solvents such as $C_1$ to $C_{10}$ aliphatic or aromatic alcohols, e.g., methanol (MeOH), ethanol (EtOH) and isopropanol (iPrOH); $C_1$ to $C_{20}$ straight or branched chain carboxylic acids or esters derived therefrom, e.g., acetic acid, propionic acid, ethyl acetate (EtOAc); dimethylformamide (DMF); tetrahydrofuran (THF); water; toluene; methylene chloride; and mixtures thereof. As appreciated in the art, varying solvents and other process conditions may affect the process steps significantly. Routine experimentation may be required to determine desired or optimal process conditions.

Preferred conditions for Step (1)(a) for reacting Compound VII with Compound VIII include basic conditions and a reaction temperature of about $-80°$ to $300°$ C., more preferred is about $-20°$ to $100°$ C.; and most preferred is about $0°$ to $40°$ C.

Preferred molar ratios of Compound VII:Compound VIII are about 1:10 to 10:1; most preferred is about 1:3 to 1:1.

Preferred conditions for Step (1)(a) for reacting Compound IX with Compound X include use of $C_1$ to $C_{10}$ aliphatic or aromatic alcohols, more preferably the solvent is the same as the nucleophile (i.e. Compound X). The most preferred solvents are MeOH, EtOH, iPrOH, and benzyl alcohol. This reaction is also preferably performed under neutral or acidic conditions and optionally in the presence of a dehydrating agent in an amount sufficient to dehydrate the carboxylic acid moiety of Compound IX. Such dehydrating agents include 4 Å molecular sieves, 3 Å molecular sieves, magnesium sulfate, dicyclohexylcarbodiimide and related carbodiimides, carbonyldiimidazole, thionyl chloride, chloroacetyl chloride, and the like.

The preferred reaction temperature for reacting Compound IX with Compound X is about the same as for reacting Compound VII with Compound VIII. Molar ratios of Compound IX:Compound X are preferably about 1:1000 to 10:1; about 1:100 to 1:10 being more preferred.

Other preferred conditions for step (1)(a) include reacting a compound of the formula VII with an alpha-halo-acetyl halide (Compound VIII) wherein Y and $Y^1$ are selected from the group consisting of chlorine, bromine, and iodine to produce a compound of the formula IX. Alternatively, VII may be allowed to react with glycine or an appropriately protected and/or activated form of glycine such that a glycine substituted dipeptide is formed (Compound IX) wherein Y is either $NH_2$ or an appropriately substituted nitrogen atom.

Other preferred conditions for the conversion of IX to VI include reacting a compound of the formula IX wherein Y is chlorine, bromine, or iodine; with a $C_1$ to $C_{10}$ alcohol under conditions which permit dehydration with formal or actual loss of water to form an ester linkage.

Preferred conditions for step (1)(b) include the same preferred molar ratios of reactants and solvents as described for step (1)(a). Also, the preferred reaction temperatures for step (1)(b) are about the same as for step (1)(a).

Other preferred conditions for step (1)(b) include reacting a compound to the formula VII with a $C_1$ to $C_{10}$ alcohol in which said alcohol is present as solvent to produce Componnd XI under conditions which permit dehydration to form an ester linkage.

Other preferred conditions for the conversion of XI to VI include reacting a compound of the formula XI (wherein $Q=OR^4$ and $R^4$ is a $C_1$ to $C_{10}$ straight or branched chain alkyl, alkylaryl, or an aryl group) with a compound of the formula VIII wherein Y and $Y^1$ are chosen from the group consisting of chloro, bromo, and iodo to produce a compound of the formula VI.

Optionally, halogen exchange (preferably with iodine) may be effected on a compound of formula VI to produce a more reactive form of Compound VI. Alternatively, Compound XI may be allowed to react with glycine or an appropriately protected and/or activated form of glycine such that a glycine substituted dipeptide (Compound VI) is formed wherein Y is either $NH_2$ or an appropriately substituted nitrogen atom.

The second ("Step 2") of the present invention comprises contacting Compound VI with a compound of the formula $$HNWW^1, \qquad (XII)$$

wherein W and $W^1$ may be the same or different and are hydrogen or a nitrogen protecting group, in the presence of an appropriate solvent, under conditions such that a compound is formed having the following formula

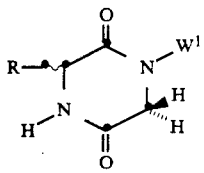

(XIII)

Appropriate solvents for step 2 are the same as described for step 1. A preferred reaction temperature for step 2 is about −80° to 300° C. with about −20° to 40° C. being more preferred. Preferred molar ratios of Compound XII:Compound VI are about 10,000:1 to 1:10 with about 1,000:1 to 1:1 being more preferred.

Other preferred conditions for Step 2 include reacting Compound VI wherein Q is $OR^4$ wherein $R^4$ is as defined hereinbefore and Y is chloro, bromo or iodo with ammonia in a $C_1$-$C_{10}$ alcohol solvent such as methanol, ethanol, phenol, benzyl alcohol, n-propanol, isopropanol, etc. Certain reactants, e.g. ammonia, can be used as solvent.

Alternatively, the cyclic dipeptide (Compound XIII) may be prepared from an ester of the linear dipeptide containing an appropriate N-terminal amino acid, and a C-terminal glycine which is itself prepared by condensation of an N-protected amino acid and an unprotected or carboxy-protected glycine.

The third step ("Step 3") of the present invention comprises reacting Compound XIII with compounds of the formula ZQ, and $Z^1Q$ wherein QH or $QW^1$ are actually or formally liberated in the reaction, in the presence of an appropriate solvent and optionally at least a catalytic amount of a suitable catalyst under conditions such that a compound is formed having the formula

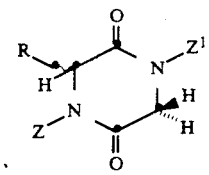

(XIV)

wherein Z, $Z^1$, R, and Q are as defined hereabove. For XIV and for preceding compounds in this process, it is preferred that R is acyloxy.

Appropriate solvents for Step 3 are the same as described for step 1 and additionally include an acyl anhydride such as

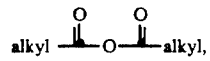

preferably wherein the alkyl groups contain 1 to 6 carbon atoms; preferred solvents are $C_1$ to $C_{20}$ straight or branched chain carboxylic acids such as acetic acid or aprotic solvents such as ethyl acetate, THF, DMF, toluene, or the like. It is preferred that Compounds ZQ and $Z^1Q$ are the same. The nature of the Q group in ZQ and/or $Z^1Q$ is generally not important so long as the Q group permits the incorporation of Z and $Z^1$ in XIV during the conversion of XIII to XIV. Preferred compounds that can be ZQ and/or $Z^1Q$ include acyloxy halides such as benzyl chloroformate, aromatic or aliphatic anhydrides or substituted aliphatic anhydrides such as and acetic anhydride and enol esters or enol acyloxy compounds such as isopropenyl acetate, ethynyl acetate or the like. For the formation of XIV from XIII, it is also preferred that ZQ and $Z^1Q$ are the same and that Z and $Z^1$ are nitrogen protecting groups. For XIV, it is more preferred when Z and $Z^1$ are the same and are acyl or acyloxy. It is also preferred that ZQ and/or $Z^1Q$ is used as the reaction's suitable solvent A large molar excess of ZQ and $Z^1Q$ to Compound XIII is therefore possible, but usually at least about 1 mole equivalent of each of ZQ and $Z^1Q$ are desired.

Preferred reaction temperature for step 3 is about −20° to 300° C. with about 50° to 150° C. being more preferred.

Preferred catalysts that are optionally used for step 3 are acid catalysts, e.g., strong acid or weak acid catalysts. Such catalysts include acetic acid, $Cu^{II}Cl_2$ and p-toluene sulfonic acid (TsOH). Preferred catalytic amounts (or more) include a molar ratio of catalyst:Compound XIII of about 1:100,000 to 10:1; especially preferred for weak acid catalysts is about 1:1,000 to 10:1 with about 1:20 to 10:1 being more preferred; especially preferred for strong acid catalysts is about 1:1000 to 1:100. In the case where $W'=Z=Z'=H$, Step 3 is not necessary and in further steps Compound XIV and XIII are the same.

The fourth step ("Step 4") of the present invention comprises contacting Compound XIV with either (a) a compound of the formula

  (XV), or (b) a compound of the formula

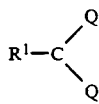

(XVI)

wherein each Q and $R^1$, independently, are as defined hereabove, in the presence of an acid or base, and a suitable solvent under conditions such that a compound is formed having the formula

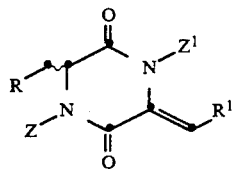

(I)

wherein R, $R^1$, Z and $Z^1$ are as defined hereabove. For I, it is preferred that R is acyloxy, $R^1$ is aryl, Z is a nitrogen protecting group and $Z^1$ is hydrogen. For I, it is more preferred that $R^1$ is acyloxy, $R^1$ is phenyl, Z is acetyl or alpha-haloacetyl and $Z^1$ is hydrogen. Suitable solvents for step 4 are the same as described for step 1.

Preferred conditions for Step 4a include reaction of XIV with a strong base such as potassium t-butoxide (KOtbu), in an aprotic solvent, and permitting the deprotonated intermediate derived from Compound XIV to react with compound XV.

Preferred conditions for Step 4b include permitting a deprotonated intermediate formed as described above to react with Compound XVI.

Preferred reaction temperatures for step 4 are about −80° to 100° C.; more preferred is about −20° to 100° C.; most preferred is about −20° to 25° C.

The molar ratio of Compound XIV to Compound XV or XVI is preferably about 1:1 to 1:10.

The fifth step ("Step 5") of the present invention is the novel hydrogenation step described in the "Summary of the Invention" section.

Suitable solvents for step 5 are the same as described for step 1. Preferred solvents include $C_1$ to $C_{10}$ alcohols, such as MeOH, EtOH, iPrOH; and DMF. Preferred reaction temperatures for step 5 are about −80° to 100° C.; more preferred is about −80° to 50° C.; most preferred is about −50° to 25° C. Lower temperatures are generally preferred to enhance diastereomeric selectivity in reduction. In step 5, hydrogen can be hydrogen gas or other source of hydrogen. Suitable catalysts for step 5 are common hydrogenation catalysts known in the art such as transition metal catalysts. Examples include palladium on carbon (Pd-C), palladium on aluminum, and the like. Molar ratio of hydrogen to Compound I are not known to be critical but typically an excess of hydrogen is used. The amount of catalyst is a catalytic amount or greater; typically a molar ratio of catalyst:Compound I of about 10,000 to 10:1 is used. The molar ratio of Compound I:hydrogen is about 1:1 to 1:10,000.

The sixth step ("Step 6") of the present invention comprises either
(a) the nucleophilic addition step described in the "Summary of the Invention" section or,
(b) contacting a compound of the formula

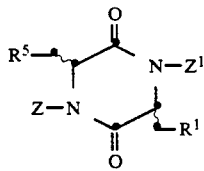

(IIa)

with a suitable nucleophile of the formula HQ in the presence of a suitable solvent and acid or base and under other conditions such that a compound is formed of the formula

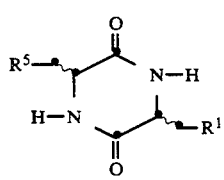

(XVII)

wherein $R^5$ is $C_1$ to $C_{10}$ acyloxy; Z is acyl, or acyloxy, $Z^1$ is acyl, acyloxy or hydrogen (preferred is hydrogen) and $R^1$ is as described hereabove. The most preferred $R^1$ is phenyl. As within the teaching of the present invention Compound XVII is understood to exist substantially or wholly as the cis derivative and in a substantially high degree of optical purity (i.e. as the LL or DD isomer).

As will be appreciated by those skilled in the art, Compound XVII can be prepared directly from I. For Z a nitrogen protecting group, loss of Z may precede or follow hydrogenation.

Suitable solvents and temperatures for step 6 are the same as for step 1. Preferred solvents for Step 6(a) are $C_1$ to $C_{10}$ alcohols such as MeOH, EtOH; iPrOH; DMF, and water. Preferred is when the compound of formula HQ and solvent are the same. Preferred bases for Step 6(a) are weak bases such as potassium carbonate, sodium carbonate, and stronger bases such as sodium methoxide, and potassium methoxide. Also tertiary amines such as trialkyl amine, for example, triethyl amine and trimethyl amine, may be used as base. Preferred molar ratios of Compound HQ:Compound II are about 1:1 to 1,000:1 with about 10:1 to 100:1 being preferred. Preferred molar amounts of acid or base to Compound II are about 1,000:1 to 1:1,000 with 1:10 to 10:1 being preferred.

Other preferred conditions for Step 6(a) include treatment of Compound II wherein Z is acyloxy or acyl, $Z^1$ is acyloxy, acyl, or hydrogen (preferably hydrogen), wherein the ability of the Z substituent to withdraw electrons is greater than the ability of the $Z^1$ substituent to withdraw electrons, R is acyloxy, and $R^1$ is aryl (preferred is phenyl), with an alcohol $R^6OH$ (including water wherein $R^6$ is H) wherein $R^6$ is hydrogen, $C_1$ to $C_{10}$ alkyl, $C_5$ to $C_{12}$ aryl, or $C_7$ to $C_{12}$ arylalkyl in the presence of a mild base such as potassium carbonate.

Preferred conditions for Step 6(b) include when $R^5$ is acyloxy and $R^1$ is phenyl in Compound XVII. Suitable nucleophiles are within the scope of those of the formula HQ. Preferred nucleophiles are nitrogen or oxygen-containing nucleophiles such as water, $C_1$ to $C_{10}$ alcohols, alkyl amines such as methyl or ethyl amine, and hydrazine or substituted hydrazines. Suitable acids are strong acids such as HCl; suitable bases are amine nucleophiles such as primary or secondary amines (e.g., ethyl amine, methyl amine, and the like), and hydrazine or substituted hydrazines (e.g., methyl hydrazine). Preferred ratios of reactants are about the same as for Step 6(a). In general, strong bases and strongly nucleophilic bases tend to favor Step 6(b) over 6(a). Preferred molar ratios of Compound IIa:compound of the formula HQ is about 1:1 to 1:1000.

The term "dipeptide" as used herein means natural and synthetic dipeptides and derivatives thereof. The compounds formed by the process of the present invention, i.e., the compounds of Formula III or XVII are useful either as active dipeptides or as intermediates for preparation therefor, or are useful intermediates for the preparation of active polypeptides and/or proteins. Such active dipeptides, polypeptides and/or proteins are useful as nutritional supplements, as therapeutic agents, and as artificial sweeteners. Preferred compounds of formula III are useful as artificial sweeteners or intermediates therefor.

It is to be understood that certain compounds described herein can exist in salt form. For example, compounds containing an amino moiety, such as Compound XI, typically readily form acid addition salts such as a hydrochloride, trifluoroacetate, and the like. The salts of such compounds are contemplated to be within the scope of the invention. If a salt form of a compound is present, it may be desirable to optionally convert the salt by simple techniques well known in the art to the free·base form of the compound.

It is generally preferred that all of the process steps described herein are carried out under an inert atmosphere, e.g., under nitrogen or argon. In some cases the presence of ambient atmosphere is not detrimental. Preferred processes of the present invention can be represented in the following schemes. The numbered compounds can be cross-referenced to the examples contained herein.

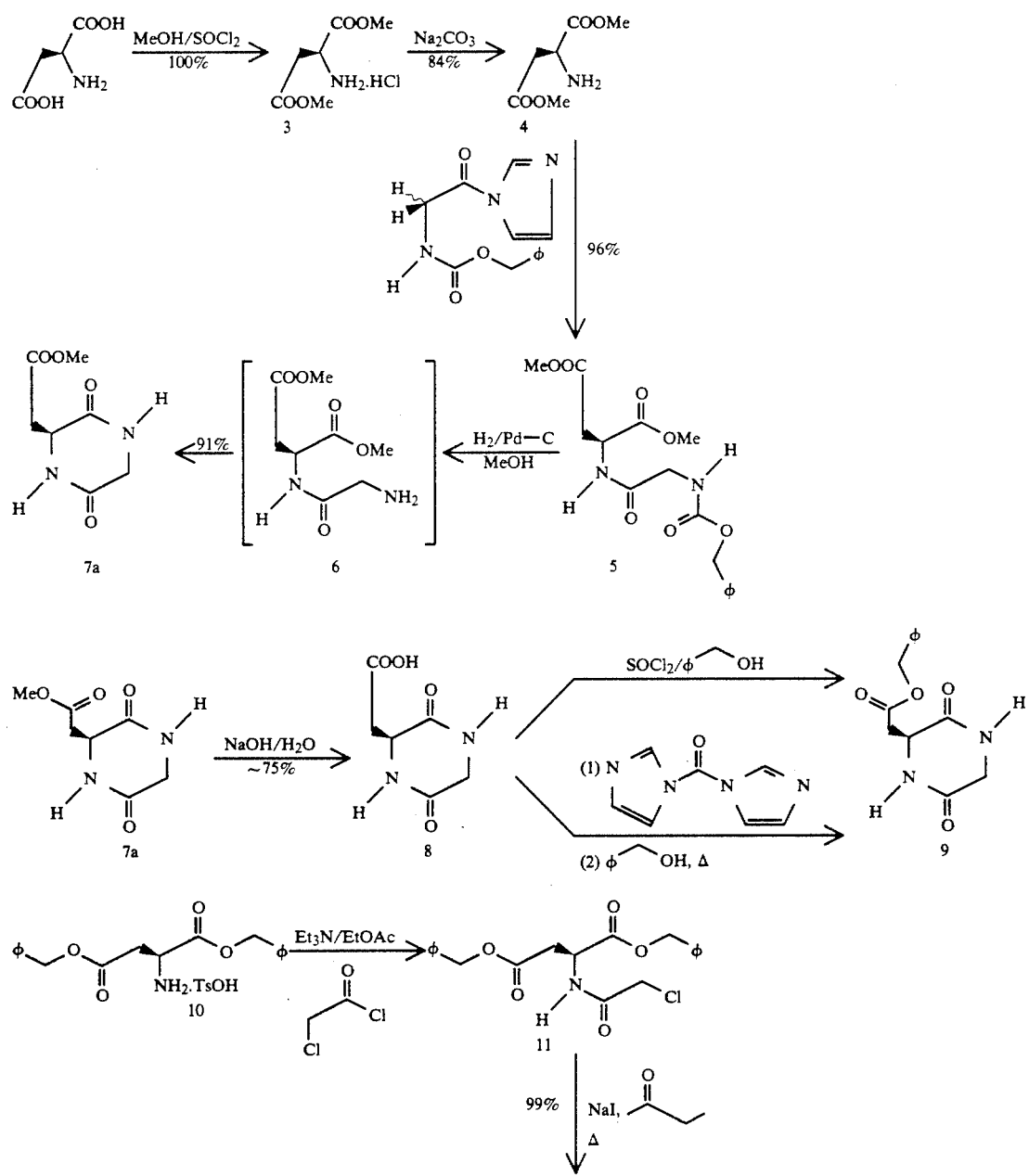

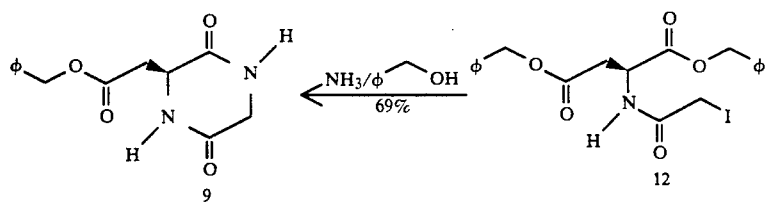
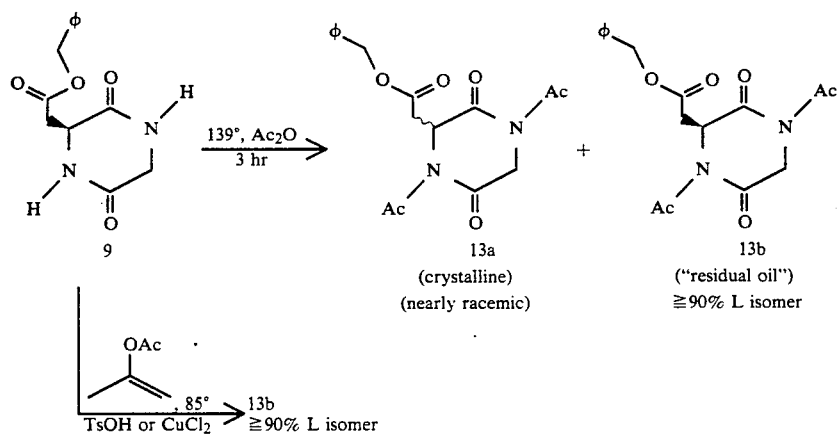
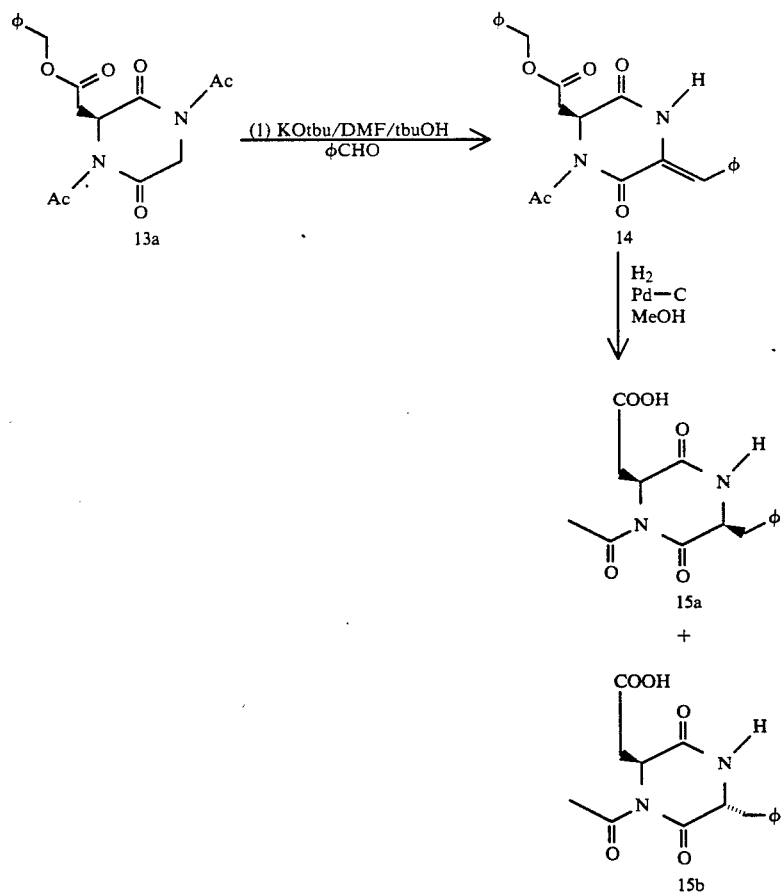

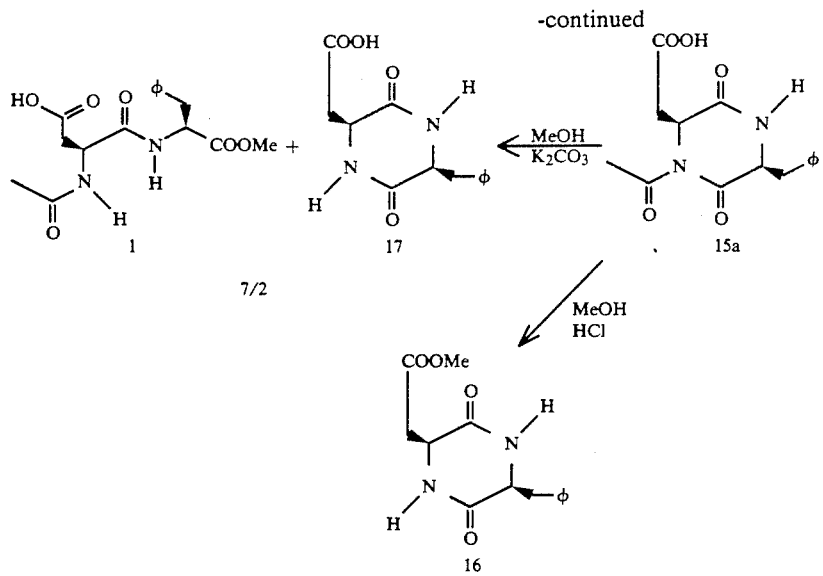

7/2

The present invention is illustrated by the following examples, however, such examples should not be interpreted as a limitation upon the scope of the present invention.

EXAMPLES

General Procedures

Melting points were determined using a Thomas Hoover capillary melting point apparatus and are uncorrected. Infrared (IR) spectra were recorded on a Perkin-Elmer Model 137 or a Nicolet Model 5DX spectrophotometer and are reported in wave numbers ($cm^{-1}$). All mass spectra were obtained using a VG Analytical Ltd. Model ZAB-1F Mass Spectrometer in EI (electron impact) and FD (field desorption) modes. Gas Chromatographic Mass Spectroscopy (GCMS) were obtained using a Finnigan 4023 GCMS equipped with a 30 m DB5 capillary column (J & W Scientific) using helium carrier gas. Optical rotations were measured using an Autopol III polarimeter manufactured by Rudolph Research.

Unless otherwise specified, all proton nuclear magnetic resonance ($^1H$ NMR) spectra were obtained on a JEOL GX-400 NMR instrument operating at 400 megahertz (MHz). This instrument is capable of a routine resolution of 0.6 hertz (Hz).

Chemical shifts are expressed in parts per million relative to internal tetramethylsilane.

High pressure liquid chromatography (HPLC) was accomplished using a Varian 5060 liquid chromatograph equipped with a Zorbax ® ODS 4.6 millimeter (mm)×25 centimeter (cm) column. Compounds were detected using a Perkin-Elmer LC-75 UV detector at 254 nanometers (nm). All injections were a 10 microliter volume.

Gas chromatography (gc) was accomplished using a Hewlett Packard 5880A instrument in capillary mode using a flame ionization detector unless otherwise specified. Hydrogen was used as a carrier gas at a flow rate of approximately 40 cm/sec. Unless otherwise specified, a 30 m DB5 column (J & W Scientific) was used for gc analyses.

All reactions were carried out under an inert atmosphere of nitrogen or argon unless otherwise specified. Anhydrous tetrahydrofuran (THF) was prepared by distillation from metallic sodium and benzophenone immediately prior to use.

All dimethylformamide (DMF) was distilled using a 1.5×48 in. Podbielniak Helipak column (90 theoretical plates) and only the constant boiling fraction (bp 45° C., 10 mm Hg) was collected. This distilled DMF was stored in the dark under a nitrogen atmosphere and over 4 A sieves. If used within one year, material prepared and stored in this fashion was found to contain less than 35 parts per million of water (Karl Fischer titration) and less than 10 parts per million of dimethyl amine as determined by cation analysis on a Dionex Model 16 ion chromatograph. The sensitivity of this ion chromatography method for dimethyl amine detection was found to be approximately 5 parts per million.

For convenience, compounds individually prepared are identified by the numeric or alpha numeric designations in parenthesis immediately following the first recitation of the compound name. These designations are also used in the flow diagram for certain preferred embodiments in the section preceding the Examples. The method designation (i.e., Method A, B, and C) are also included for easy cross-reference to said flow diagrams.

Example 1

L-Dimethylaspartate hydrochloride (3)

Thionyl chloride (124 mL, 1.7 mol) was added to a stirred suspension of L-aspartic acid (102.4 g, 0.769 mol) and methanol (1 liter, 1L) at a temperature of −10° to 0° C. After the addition of thionyl chloride was complete (about 20 minutes), the now homogeneous solution was allowed to warm to room temperature and was left to stir overnight. The reaction solution was then concentrated in vacuo. The resulting semi-solid mass was redissolved in methanol (250 mL) and was reconcentrated in vacuo (about 1 mm, about 40° C., 5 hours) to provide product 3 (152.15 g, 0.770 mol, 100%). In a repetition of this experiment (100-g scale) a 99% yield was obtained. A satisfactory $^1H$ NMR analysis was obtained for the hygroscopic product 3.

FDMS: 162 (—Cl)

Analysis: Cal. for $C_6H_{12}NO_4Cl$: C, 36.47; H, 6.12; N, 7.09; Cl, 17.94 Found: C, 36.31; H, 6.08; N, 6.84; Cl, 18.02

Optical Rotation: $[\alpha]_D^{25} = +14\ 80°$ (c $=0.906$, methanol)

Example 2

Dimethylaspartate (4)

Diethylaspartate hydrochloride (3, 85.31 g, 0.432 mol) was dissolved in a saturated solution of aqueous sodium carbonate (200 mL) and extracted with ethyl acetate (10×250 mL) in a separatory funnel. The combined organic phases were dried by filtration through magnesium sulfate and sodium sulfate and concentrated in vacuo to provide dimethyl aspartate (58.73 g, 0.364 mol, 84%) as a pale yellow oil. This material provided satisfactory $^1$H NMR data and was used immediately in the preparation of N-benzyloxycarbonylglycyl-L-$\alpha$-aspartic acid dimethyl ester (5).

GCMS: M+1=162 (NH$_3$-CIMS)

Example 3

N-Benzyloxycarbonyl-glycyl-L-$\alpha$-aspartic acid dimethyl ester (5)

Carbonyldiimidazole (62.18 g, 0.384 mole) was added to a solution of N-benzyloxycarbonylglycine (81.56 g, 0.390 mol) in anhydrous tetrahydrofuran (THF, 500 mL). The resulting solution was stirred for four hours at room temperature before cooling to a temperature of approximately 5° C. with a cold acetone bath. A solution of dimethylaspartate (58.11 g, 0.360 mol) in THF (100 mL) was added to the cold solution in one portion. The cooling bath was removed from the resulting solution (19° C.) and the reaction mixture was allowed to stir overnight. Water (50 mL) was added to the reaction mixture and the resulting solution was concentrated in vacuo to provide a viscous oil. This oil was added to a separatory funnel containing ethyl acetate (1.3 L) and 1N aqueous HCl (250 mL). Concentrated HCl (about 45 mL) was added until the pH of the aqueous phase was 1. The aqueous phase was removed and the resulting organic phase was extracted sequentially with 1N HCl (250 mL), water (150 mL), half-saturated sodium carbonate (2×250 mL), and brine (250 mL). The resulting organic phase was dried by filtration through magnesium sulfate and sodium sulfate and concentrated in vacuo to provide product 5 (121.94 g, 0.346 mol, 96%) as a viscous oil. Satisfactory $^1$H NMR data were obtained for this material.

FDMS: M+ =352

Example 4

Cyclo-glycyl-L-$\alpha$-aspartic acid $\beta$-methyl ester (7a)

N-Benzyloxycarbonyl-glycyl-L-$\alpha$-aspartic acid dimethyl ester (5, 80.96 g, 0.230 mol) was dissolved in methanol containing 5% palladium on carbon (10.2 g). Hydrogen was then introduced at atmospheric pressure into the stirred reaction vessel at a rate slightly in excess of the rate of consumption. A room temperature water bath was applied to the reaction vessel to prevent excessive heating of the solution. Hydrogen uptake by the reaction had ceased within 45 minutes. After purging the reaction vessel with argon, the resulting mixture was filtered through celite and diluted to a final volume of two liters with methanol. The resulting solution was allowed to stand at room temperature for 21 hours to allow for formation and crystallization of the diketopiperazine product 7a. The product 7a (23.70 g, 0.127 mol, melting point (mp) 201°–203° C.) was filtered and the resulting filtrate was set aside for an additional four days. As a minimal amount of further precipitation occurred, the solution containing the filtrate was concentrated in vacuo to a volume of 300 mL and cooled to 0° C. Filtration of the resulting precipitate provided a second crop of diketopiperazine 7a (15.47 g, 0.0831 mol, mp 202°–204° C.) for a combined yield of 91%. Satisfactory $^1$H NMR data were obtained for both preparations of this product.

FDMS: M+ =186

IR (KBr): $\nu=3570-2890$, 1754, 1690, 1670, 1470, 1440

Analysis: Cal. for C$_7$H$_{10}$N$_2$O$_4$: C, 45.16; H, 5.41; N, 15.05 Found: C, 45.12, H, 5.44; N, 15.07

Optical Rotation: $[\alpha]_D^{25} = +52.36$ (c$=0.972$, H$_2$O, first crop) $[\alpha]_D^{25} = +51.23$ (c$=1.095$, H$_2$O, second crop)

Example 5

Cyclo-glycyl-L-$\alpha$-aspartic acid (8)

A freshly prepared solution of 2N aqueous sodium hydroxide (72.5 mL) was added to a solution of methyl ester 7a (26.44 g, 0.142 mol) in distilled water (600 mL). After a period of 30 minutes at room temperature, HPLC analysis indicated that only 2% of the originally introduced methyl ester remained in the reaction mixture. After a total reaction time of 50 minutes, the reaction mixture was neutralized to a pH of 2.5 by addition of concentrated HCl (about 13 mL) followed by addition of 2N HCl (about 2 mL). The solvent was removed in vacuo to a volume of approximately 150 mL (pH=2) and the resulting solution was left at 4° C. overnight. The crystallized product (14.79 g, 0.0859 mol, 60.5%, mp 214°–215° C.) was removed by filtration. A second crop of the Product 8 (4.00 g, 0.0232 mol, 16.4%) was obtained upon concentration of the filtrate to dryness and crystallization of the resulting material from distilled water (40 mL) at 4° C. Elemental analysis indicated that the first crystalline crop of acid 8 contained approximately 0.5% chlorine while the second crop contained approximately 3% chlorine. Both preparations of this material provided satisfactory $^1$H NMR data.

FDMS: M+ =172

IR (KBr): $\nu=3330-2860$, 2630-2350, 1709, 1670, 1650

Analysis: Cal. for C$_6$H$_8$N$_2$O$_4$: C, 41.86; H, b 4.68; N, 16.27 Found: C, 41.61; H, 4 68; N, 16.07; Cl, 0.53 (first crop) Found C, 40.10; H, 4.58; N, 15.52; Cl, 3.38 (second crop)

Optical Rotation: $[\alpha]_D^{25} = +51.16$ (c$=0.995$, H$_2$O, first crop) $[\alpha]_D^{25} = +44.37$ (c$=1.03$, H$_2$O, second crop)

Example 6

Cyclo-qlycyl-L-u-aspartic acid $\beta$-benzyl ester (9), Method A

Thionyl chloride (4.6 mL, 0.063 mol) was added to a suspension of cyclo-glycyl-L-$\alpha$-aspartic acid (9.83 g, 0.0571 mol, 0.53% Cl content, $[\alpha]_D^{25} = +51.16$; c$=0.995$, H$_2$O) in benzyl alcohol (200 mL). The reaction mixture was warmed to a temperature of 70° C. and stirred for 1 hour. The reaction mixture was concentrated in vacuo (0.5 mm, 1.5 hr., 70° C.) and the resulting solid was triturated with toluene (3×100 mL) to provide the crude crystalline product 9 (7.7 g, about 0.029 mol, about 51%). This material (7.12 g) was further purified by recrystallization from hot methanol (1 L). The final recrystallized yield was 40% (5.48 g, $[\alpha]_D^{25} = +52.05$; c$=0.244$, acetic acid (HOAc). Satisfactory $^1$H NMR data were obtained for this material.

Example 7

Cyclo-glycyl-L-α-aspartic acid β-benzyl ester (9), Method B

Carbonyldiimidazole (18 g, 0.11 mol) was added to a stirred suspension of cyclo-glycyl-L-α-aspartic acid (8, 15 g, 0.087 mol, 0.58% Cl, $[\alpha]_D^{25} = +52.87$; C=1, $H_2O$) in DMF (300 mL). After a period of approximately five minutes the reaction mixture became homogeneous and $CO_2$ evolution moderated. Distilled benzyl alcohol (30 mL, 0.29 mol) was then added to the reaction mixture and the resulting solution was heated at 60° C. for 3.5 hours. The reaction mixture was left to stir overnight at room temperature. The resulting solution was reheated at 60° C. for an additional 30 minutes and was then concentrated to near dryness in vacuo. The resulting residue was treated with ether (800 mL) and cooled at approximately 0° C. for 5 hours. The precipitated crystals (20.9 g) were removed by filtration and product 9 (14.8 g, 0.056 mol, 65%, mp 205-207 dec.) was obtained after recrystallization of this precipitate from hot methanol (2 L). Satisfactory $^1$H NMR data were obtained for this material.

FDMS: M+ =262

Optical rotation: $[\alpha]_D^{25} = +54.17$ (c=0.216, acetic acid)

Example 8

N-α-Chloroacetyl-L-aspartic acid dibenzyl ester (11)

A solution of L-aspartic acid dibenzyl ester p-toluene sulfonic acid salt (150 g, 0.309 mol) and distilled triethylamine (93 mL, 0.67 mol) in ethyl acetate (1.1 L) was cooled to 0° C. Chloroacetyl chloride (25.5 mL, 0.32 mol) was added to the resulting solution at a rate such that the reaction temperature did not exceed 10° C. The reaction mixture was then stirred at room temperature for a period of 1.5 hours. The resulting heterogeneous mixture was filtered to remove triethylamine salts. The organic filtrate was sequentially extracted with aqueous 1N HCl (2×250 mL), water (about 300 mL), half-saturated aqueous sodium carbonate (250 mL), water (about 300 mL), and brine (about 300 mL). The organic phase was dried over magnesium sulfate and concentrated in vacuo to provide product 11 (115.6 g, 0.296 mol, 96%) as a viscous brown oil which crystallized on standing. Satisfactory $^1$H NMR data were obtained for this material. This material was not further purified but was instead used directly in the preparation of iodide 12.

FDMS: M+ =389

Example 9

N-α-Iodoacetyl-L-aspartic acid dibenzyl ester (12)

A solution of N-α-chloroacetyl-L-aspartic acid dibenzyl ester (111 g, 0.285 mol) and sodium iodide (59.5 g, 0.40 mol) in 2-butanone was heated at reflux for a period of 1.5 hours. The reaction mixture was concentrated to dryness and the residue was added to a separatory funnel containing ethyl acetate (about 500 mL). The aqueous phase was removed and the organic phase was first extracted with brine (about 250 mL) and then dried over sodium sulfate. The resulting solution was then concentrated in vacuo to provide product 12 (136 g, 0.283 mol, 99%) as a viscous brown oil which slowly crystallized over a period of several days at room temperature. Satisfactory $^1$H NMR data were obtained for this material. This material was not further purified but was instead used directly in the preparation of 9.

FDMS: M+ =481

EXAMPLE 10

Cyclo-glycyl-L-α-aspartic acid β-benzyl ester (9), Method C

Iodide 12 (5.0 g, 0.0104 mol) was added to a 25° C. solution of distilled benzyl alcohol (50 mL) which had been previously saturated with ammonia gas. After a period of two hours, the resulting mixture was filtered and the collected precipitate was washed with several portions of methanol. This precipitate was dried to constant weight (1.3 g, 0.0050 mol, 48%) to provide the crystalline product 12 (mp 209°-210° C., dec.). Satisfactory $^1$H NMR data were obtained for this material.

FDMS: M+ =262

IR(KBr): $\nu$=3280-2860, 1740, 1680

Analysis: Calc. for $C_{13}H_{14}N_2O_4$: C, 59.54; H, 5.38; N, 10.68 Found: C, 59.43; H, 5.40; N, 10.78

Optical Rotation: $[\alpha]_D^{25} = +56.50$ (c=0.2, acetic acid)

This crystalline product was estimated to contain at least 98% of the L-isomer by GC analysis on a Chirasil-Val ™ capillary column. The filtrate from the above filtration was concentrated in vacuo to provide a solid resiude (4.1 g) which was found to contain 14.1% by weight of 9 by HPCL analysis. Thus, the total yield for 9 prepared by the above method was 69%. GC analysis suggested that the ester 9 in this solid residue contained up to 8% of the D-isomer.

Example 11

N,N'-Diacetyl-cyclo-glycyl-L-α-aspartic acid β-benzyl ester (13), Method A

A mixture containing cyclo-glycyl-L-α-aspartic acid β-benzyl ester (prepared by Method B, mp 205-207 dec., $[\alpha]_D^{25} = +25.17$; C=0.216, acetic acid; 10.42 g, 0.0397 mol) and distilled acetic anhydride (200 ml) was heated at reflux (about 139° C.) for a period of 2.5 hours. The solvent was removed under high vacuum (about 0.5 mm, about 50° C.) over a period of approximately three hours to provide the crude product (14.26 g). This material (14.05 g) was further purified by crystallization from hot ethyl acetate (50 mL) and heptane (160 mL). Upon filtration, three was obtained at 62% yield of crystalline material (13a, 8.50 g, 0.243 mol, mp 104-105). Upon concentration of the filtrate in vacuo, there was obtained a viscous oil (13b, 4.75 g, 0.0137 mol, 35%) which slowly crystallized over a period of several months on storage at −20° C. Residual oil (13b) and crystalline material (13a) provided $^1$H NMR data which were essentially identical and consistent with the desired product 13. Crystalline material (13a, mp 104-105) was used in all subsequent experiments. Analytical data for 13a are outlined below.

FDMS: M+ =346

IR(KBr): $\nu$=3080-2940 (w), 1725 (vs)

Analysis: Cal. for $C_{17}H_{18}N_2O_6$: C, 58.96; H, 5.24; N, 8.09 Found: C, 58.95; H, 5.25; N, 7.86

Subsequent to its preparation and use, the crystalline material from this preparation (13a) was found to contain approximately 40-45% of the D-isomer.

Example 12

N,N'-Diacetyl-cyclo-glycyl-L-α-aspartic acid β-benzyl ester (13b), Method B

A mixture containing cyclo-glycyl-L-α-aspartic acid β-benzyl ester (prepared by Method B, mp 205–207 dec., $[\alpha]_D^{25} = +54.17$; c=0.216, acetic acid; 1 g, 0.0038 mol), p-toluene sulfonic acid (5 mg) and isopropenyl acetate (50 mL) was heated at 85° C. for eight hours until a clear solution had resulted. The resulting solution was concentrated in vacuo to provide Product 13b as a viscous oil which was slow to crystallize. $^1$H NMR analysis indicated that N,N'-diacetyl-cyclo-glycyl-L-α-aspartic acid β-benzyl ester (13b) was the major product (several other acetyl containing impurities were observed). $^1$H NMR analysis using the chiral shift reagent (−) 2,2,2-trifluoro-1-(9-anthryl)ethanol did not detect the presence of any of the D isomer in this material. However, analysis by GC suggested the presence of up to 10% of the D isomer in this material.

Example 13

N,N'-Diacetyl-cyclo-glycyl-L-α-aspartic acid β-benzyl ester (13b), Method C

A stirred suspension of cyclo-glycyl-L-α-aspartic acid β-benzyl ester (prepared by Method B, mp 205–207 dec., $[\alpha]_D^{25} = +54.17$; c=0.216, acetic acid, 0.5 g, 0.019 mol), cupric chloride (100 mg, 0.7 mmol) and isopropenyl acetate (50 mL) was heated at 85° C. for 30 hours. The reaction mixture was concentrated in vacuo and then dissolved in ethyl acetate. The organic phase was extracted first with saturated aqueous sodium bicarbonate and then with water. The organic phase was dried over sodium sulfate and concentrated in vacuo to provide N,N'-diacetyl-cyclo-glycyl-L-α-aspartic acid β-benzyl ester (13b, 1.2 g) as a viscous oil. Satisfactory $^1$H NMR data were obtained for this material (the presence of a hydrocarbon containing impurity, perhaps derived from the solvent, was also indicated). $^1$H NMR analysis using the chiral shift reagent (−) 2,2,2-trifluoro-1-(9-anthryl)ethanol did not detect the presence of any of the D isomer in this material. However, analysis by GC suggested the presence of up to 10% of the D isomer in this material.

Example 14

Unsaturated diketopiperazine (14)

A solution containing N,N'-diacetyl-cyclo-glycyl-L-α-aspartic acid β-benzyl ester (crystalline material prepared by Method A, mp 104–105, 5.62 g, 0.0162 mol), benzaldehyde (3.4 mL, 0.0335 mol) and DMF (15 mL) was chilled to −5° C. A freshly prepared solution of potassium t-butoxide in distilled, anhydrous t-butyl alcohol (1.49M, about 10.8 mL, about 0.016 mol) was then added at a temperature of between −5° and 5° C. over a period of approximately 10 minutes. The reaction mixture was then stirred for approximately 20 minutes without external cooling as the reaction temperature rose to 20° C. Acetic acid (0.25 mL, 0.0044 mol) was then added to the reaction mixture and the solvent was removed from the resulting mixture in vacuo. The resulting residue was dissolved and suspended in ethyl acetate (150 mL) and the ethyl acetate phase was sequentially extracted with water (75 mL), half-saturated sodium bicarbonate (2×75 mL), water (100 mL) and brine (75 mL). The organic phase was dried by filtration through magnesium sulfate and sodium sulfate and concentrated in in vacuo to provide the unsaturated product 14 (6.86 g) which was shown to contain traces of ethyl acetate and benzaldehyde by $^1$H NMR. This material was not purified further but was instead reduced directly to the cis-diketopiperazine 15a.

FDMS: M+ =392

Example 15

N-Acetyl-cyclo-L-α-aspartyl-L-phenylalanine (15a)

Hydrogen gas (1 atm) was introduced into a reaction vessel containing diketopiperazine 14 (3.94 g, about 0.010 mol), methanol (90 mL) and 5% palladium on carbon (0.84 g). The reaction mixture was stirred at room temperature and maintained under a hydrogen atmosphere for 28.5 hours. The resulting solution was first purged with argon and then filtered through celite. The filtrate was concentrated in vacuo to provide the crude product as a viscous oil (2.61 g). FDMS suggested that a single product was present with a molecular weight of 304. $^1$H NMR suggested the presence of two isomers in a ratio of approximately 3 to 1. A portion of the reaction product (2.41 g) was purified by medium pressure column chromatography on silica gel (200 g, E. Merck, 230–400 mesh) using 5% acetic acid in ether (2 L) as eluent. The early fractions contained the minor isomer 15b (0.3 g) as the higher $R_f$ component. The major isomer was collected as a mixed fraction (about 0.48 g, containing the major and minor isomers in a ratio of approximately 4 to 1) and as a "center cut" which contained the pure isomer (0.963 g, 0.0032 mol, about 34%). The chromatographed yield for the major isomer 15a for both the benzaldehyde condensation and the reduction was approximately 44% (including the mixed fraction from the above chromatography). The $^1$H NMR data for the major isomer 15a are consistent with its assignment as the cis-diketopiperazine isomer.

FDMS (major isomer): M+ =304
FDMS (minor isomer): M+ =304

Example 16

N-Acetyl-L-α-aspartyl-L-phenylalanine methyl ester (1)

Anhydrous potassium carbonate (490 mg, 3.55 mmol) was added to a solution of 15a (363.6 mg, 1.19 mmol) in methanol. The resulting mixture was stirred for a period of 20 minutes and was then neutralized to a pH of approximately 2 (moist, narrow range pH paper) by addition of 1N aqueous HCl (about 8 mL). The resulting solution was concentrated in vacuo to provide a white solid (0.919 g). Analysis of this material by $^1$H NMR indicated that, of the organic products, only diketopiperazine 17 and N-acetyl-L-a-aspartyl-L-phenylalanine methyl ester (1) were present in a ratio of approximately 2 to 7. A portion of the crude product (897.7 mg) was added to a separatory funnel containing ethyl acetate (75 mL) and 0.5N aqueous HCl (50 mL). The organic phase was removed and the aqueous phase was reextracted with ethyl acetate (50 mL). The organic phases were combined and filtered through sodium and magnesium sulfate. The resulting solution was concentrated in vacuo to provide a white solid which was shown by $^1$H NMR to contain diketopiperazine 17 and 1 in a ratio of 1 to 6 (0.220 g, ca.0.65 mmol, ca. 50%). An analytical sample of 1 was prepared by careful medium pressure chromatography of the organic products from this reaction on silica gel using 10 to 20% acetic acid in ether as eluent. The $^1$H NMR of the major component from this reaction, 1, was identical to the ¹H NMR obtained for a sample of N-acetyl-L-α-aspartyl-L-phenylalanine methyl ester which had been previously prepared from L-α-aspartyl-L-phenylalanine methyl ester.

FDMS: M+ =336

Optical Rotation $[\alpha]_D^{25} = -2.8$ (c=1.0. methanol) $[\alpha]_D^{25} = -36.8$ (c=1.029, methanol)*

*This reference sample was prepared by treatment of aspartyl-phenylaline methyl ether with acetic anhydride.

Example 17

GC Method for Determination of the Optical Purity of the Aspartic Acid Subunit in Various Intermediates A sample of the aspartic acid containing derivative (about 10-20 mg) and aqueous 6N HCl (about 25 mL) was heated at reflux for 18-22 hours. A homogeneous solution usually resulted. The reaction mixture was cooled and the resulting solution was concentrated to dryness under high vacuum at a bath temperature of 35°-55° C. A portion of the hydrolysis product (about 10 mg) and 6.1 N isopropanolic HCl (about 1-2 mL, previously prepared by addition of HCl gas to isopropanol) were heated in a sealed Reacti-Vial ™ at approximately 90°-100° C. for four hours. Solvent was removed from the esterified product by passing a stream of nitrogen over the heated (55° C.) reaction mixture. The resulting dry product was dissolved at room temperature in a methylene chloride solution (about 1 mL) containing 30% trifluoroacetic anhydride (v/v). The resulting solution was allowed to stand at room temperature for a period of approximately one hour. Solvent was then removed from the product by passing a stream of nitrogen (or argon) over the reaction mixture. The resulting oil which contained the N-trifluoroacetyl-aspartic acid diisopropyl ester was dissolved in methylene chloride (about 0.5 mL) under an inert atmosphere. This material was analyzed immediately by gc using a 25-meter Chirasil-ValT, (obtained from Applied Science), GC column (isothermal, 140° C., hydrogen carrier gas) using conditions which have been previously described in the art for the analysis of amino acid derivatives; e.g., (a) I. M. Moodie, J. Burger, *J. High Res Chromatog. & Chromatog. Comm.*, 4, 218 (1982); (b) H. Frank, E. Bayer, ibid., 411 (1979) and references cited therein. A solution containing N-trifluoroacetyl- D,L-aspartic acid diisopropyl ester was used to identify the individual peaks in the GC analyses. The NMR analysis for compound 13a was performed in accordance with the procedures disclosed in W. H. Pirkle, D. L. Sikkenga, *J. Org. Chem.*, 42, 384 (1977). This NMR method using the chiral shift reagent (−)-2,2,2,-trifluoro-1(9-anthryl) ethanol is estimated to have a threshold for detection of the D-isomer of 13 of less than 10%.

The results of the gc analyses are presented below in tabular form.

| Intermediate | % L | % D |
|---|---|---|
| 7a | | |
| (cyclo-glycyl-L-α-aspartic acid β-methyl ester, mp 203, $[\alpha]_D^{25}$ = +50.00, c = 1, H₂O | 96.10 | 3.90 |
| 8 | | |
| (clyclo-glycyl-L-α-aspartic acid, $[\alpha]_D^{25}$ = +52.87, c = 1, H₂O | 95.51 | 4.49 |
| 9 (Method B) | | |
| (cyclo-glycyl-L-α-aspartic acid, β-benzyl ester, $[\alpha]_D^{25}$ = +54.17, c = 0.216, HOAc) | 95.97 | 4.03 |

-continued

| Intermediate | % L | % D |
|---|---|---|
| 9 (Method C) | | |
| $[\alpha]_D^{25}$ = +56.50, c = 0.2, HOAc) | 97.86 | 2.14 |
| (solid residue from crystallization in Method C) | 91.77 | 8.23 |
| 12 | | |
| (acyl iodide) | 95.84 | 4.16 |
| 13a | | |
| (crystalline diacetate, mp. 104-105, Method A) | 60.44 | 39.56 |
| [crystalline diacetate, (NMR Analysis, mp. 104-105, Method A)] | 57-59 | 41-43 |
| 13b | | |
| (diacetate, Method C) | 89.39 | 10.61 |
| (diacetate, Method C) | 89.12 | 10.88 |
| 14 | | |
| (benzaldehyde condensation product) | 55.78 | 44.22 |
| 1 | | |
| ("authentic" material prepared previously, $[\alpha]_D^{25}$ = −36.8, c = 1.029, methanol) | 94.10 | 5.90 |
| (prepared from optically impure 14, as reported in this work $[\alpha]_D^{25}$ = −2.8, c = 1, methanol) | 57.23 | 42.77 |

Example 18

L-α-aspartyl-L-phenylalanine (2)

A solution of N-acetyl-L-α-aspartyl-L-phenylalanine methyl ester (1, 1.51 g, 4.49 mmol) in aqueous 1N HCl (100 mL) was refluxed for 1 hour and 50 minutes. The resulting solution was concentrated in vacuo to provide the solid reaction products (1.61 g). External standard HPLC analysis indicated that this mixture of reaction products contained 16 weight percent of dipeptide 2. The generation of dipeptide 2 from acid hydrolysis of 1 was confirmed by FDMS and accurate mass measurements.

FDMS: M+ =280

Accurate Mass: Calc. for $C_{13}H_{17}O_5N_2$: 281.1133 (M+1) Found: 281.1134 (M+1)

I claim:

1. A process comprising contacting a compound of the formula

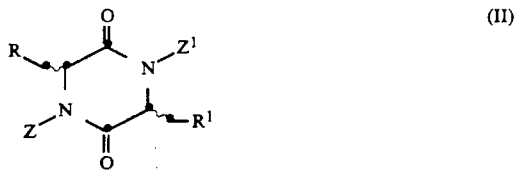

(II)

with a nucleophile, in the presence of an appropriate base, under conditions such that a compound is formed of the formula:

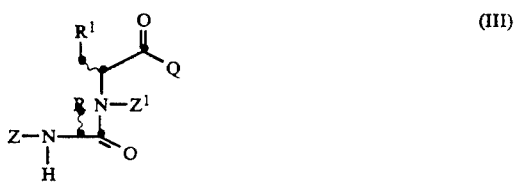

(III)

wherein R and R¹ are different and are each, independently, hydrogen, alkyl, hydroxy, aryl, C₁ to C₁₀ substituted alkyl, C₁ to C₁₀ alkoxy, C₇ to C₁₂ substituted arylalkyl, $C_1$ to $C_{10}$ acyl, $C_1$ to $C_{10}$ carboxyalkyl or $C_1$ to $C_{10}$ acyloxy; Z is a nitrogen-protecting group; $Z^1$ is hydrogen or a nitrogen-protecting group provided that the ability of the Z substituent to withdraw electrons is greater than that of the $Z^1$ substituent; and Q is a residue of a nucleophile.

2. The process of claim 1 wherein said appropriate base is potassium carbonate or sodium carbonate.

3. The process of claim 1 wherein the diastereomeric purity and optical purity of Compounds II and III are at least about 90% and wherein Compound II exists predominantly as the cis diastereomer.

4. The process of claim 1 carried out a temperature of about $-20°$ to $100°$ C.

5. The process according to claim 1 wherein said appropriate base is a weak base.

6. A process comprising contacting a compound of the formula

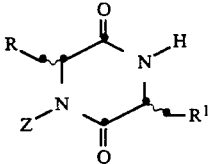

with a nucleophile, in the presence of an appropriate base, under conditions such that a compound is formed of the formula:

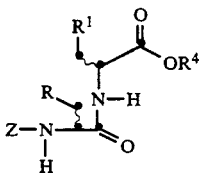

wherein R is $C_1$ to $C_{10}$ acyloxy, $R^1$ is aryl, Z is acyl or acyloxy, and $R^4$ is hydrogen, alkyl, or aryl.

7. The process of claim 6 wherein Z is acetyl or alpha-haloacetyl.

8. The process of claim 6 wherein R is $C_1$ to $C_{10}$ acyloxy, $R^1$ is phenyl, $Z^1$ is hydrogen, Z is acetyl, and Q is $-OR^4$, wherein $R^4$ is H or $C_1$ to $C_6$ alkyl.

* * * * *